(12) United States Patent
Collado et al.

(10) Patent No.: US 7,753,896 B2
(45) Date of Patent: Jul. 13, 2010

(54) DRAPEABLE ABSORBENT ARTICLE

(75) Inventors: Santos H. Collado, Las Pinas (PH);
Maria Elaine P. de Velez, Quezon (PH);
Jutta S. Haarer, Princeton, NJ (US);
Barbara Ann Ludwig, Basking Ridge, NJ (US); Ana Maria Elena R. Marcelo, North Brunswick, NJ (US); H. Michael Moscherosch, Doylestown, PA (US); Rita Renee Pilate, Washington Crossing, PA (US); Jennifer L. Sturgeon, Long Valley, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 379 days.

(21) Appl. No.: 10/025,299

(22) Filed: Dec. 19, 2001

(65) Prior Publication Data

US 2003/0114822 A1 Jun. 19, 2003

(51) Int. Cl.
*A61F 13/15* (2006.01)
(52) U.S. Cl. .................... 604/385.01; 604/385.101; 604/374; 604/375; 604/378
(58) Field of Classification Search ............ 604/385.01, 604/385.16, 385.22, 400, 384, 374, 375, 604/377, 367, 366, 378, 385.101, 385.23; 442/224, 246, 414
See application file for complete search history.

(56) References Cited

U.S. PATENT DOCUMENTS

| | | | |
|---|---|---|---|
| 3,929,135 A | 12/1975 | Thompson | |
| 4,589,876 A | 5/1986 | Van Tilburg | |
| 4,608,047 A | 8/1986 | Mattingly | |
| 4,609,518 A | 9/1986 | Curro | |
| 4,687,478 A | 8/1987 | Van Tilburg | |
| 4,773,904 A | 9/1988 | Nakanishi | |
| 4,801,494 A * | 1/1989 | Datta et al. .................. | 442/352 |
| 4,900,320 A | 2/1990 | McCoy | |
| 4,950,264 A * | 8/1990 | Osborn, III ............ | 604/385.08 |
| 5,383,869 A * | 1/1995 | Osborn, III ............ | 604/385.04 |
| 5,607,415 A | 3/1997 | Datta et al. | |
| 5,910,137 A | 6/1999 | Clark et al. | |
| 6,114,595 A | 9/2000 | Moore et al. | |
| 6,177,605 B1 | 1/2001 | Trombetta et al. | |
| 6,582,411 B1 * | 6/2003 | Carstens et al. ........ | 604/385.01 |

FOREIGN PATENT DOCUMENTS

| | | |
|---|---|---|
| EP | 625602 A1 | 11/1994 |
| EP | 0 685 214 A2 | 12/1995 |
| EP | 0705583 A1 | 4/1996 |
| EP | 0705586 A1 | 4/1996 |
| EP | 1 029 522 A2 | 8/2000 |
| EP | 1077052 A1 | 2/2001 |
| EP | 1088536 A2 | 4/2001 |
| EP | 1 108 406 A2 | 6/2001 |
| EP | 1323398 B1 | 6/2006 |
| MY | 104766 A | 5/1994 |
| NZ | 236101 | 10/1993 |
| WO | 1993021879 A1 | 11/1993 |
| WO | WO 96/10978 | 4/1996 |
| WO | WO 98/09593 | 3/1998 |
| WO | WO 99/25290 A1 | 5/1999 |
| WO | 2000072790 A1 | 12/2000 |

OTHER PUBLICATIONS

CN2433994Y, Chinese Utility Model, believed to be filed Aug. 10, 2000.
European Search Report dated Mar. 23, 2004, for corresponding EP application 02028260.4.

* cited by examiner

*Primary Examiner*—Jacqueline F. Stephens

(57) ABSTRACT

An absorbent article having a silhouette including a first end, a second end, wherein the second end being in opposite relation to the first end, and a first longitudinally extending edge opposed to a second longitudinally extending edge, the first and second longitudinally extending edges connecting the first end and the second end; and a layered portion having a body-facing layer and a garment-facing layer, wherein the absorbent article is drapeable.

3 Claims, No Drawings

DRAPEABLE ABSORBENT ARTICLE

FIELD OF THE INVENTION

The invention relates to absorbent articles for use with undergarments or other clothing, such as panty hose, swimsuits, or leotards. In particular, the absorbent articles of the present invention are drapeable.

BACKGROUND OF THE INVENTION

Disposable absorbent articles, such as pantiliners, sanitary napkins, interlabial devices, adult incontinence devices and diapers are well known in the art. These articles typically have a fluid permeable body-facing side and fluid impermeable garment facing side. Additionally, such articles may include an absorbent layer for retaining fluids therebetween.

Anatomical adaptation of an absorbent article may increase comfort to the wearer. That is, movement by the wearer may cause the absorbent article to conform to the geometry of the space between the wearer's thighs. In contrast, if the absorbent article is stiff to begin with, the wearer may experience discomfort and be conscious of the absorbent article. Additionally, if such an article bunches, there is a tendency to maintain its resulting distorted shape, thereby providing inadequate protection.

Various methods have been used to improve the flexibility of absorbent articles. For example, reducing the amount of absorbent material, using less stiff resilient materials and using thinner materials have been disclosed as possible solutions to the improving the flexibility of absorbent articles. See, for example, PCT Application No. WO 98/09593 to Gilman, which discloses a thin absorbent article that has a thickness of less than five millimeters and a crush recovery value of at least about fifteen mm.

EP 1077052 (Lariviere et al.) discloses using preferential bending zones extending along the longitudinal axis of an absorbent article together with a pair of longitudinal adhesive zones that register with the preferential bending zones to improve flexibility.

Another method that has been disclosed to improve flexibility is increasing the elasticity of the article. See, for example, U.S. Pat. No. 4,773,904 (Nakanishi et al.) and PCT Application No. WO 96/10978 (Palumbo et al.). In EP 0705583 and EP 0705586 (both to Querqui), the purported flexible absorbent article is disclosed as being elastically stretchable while having a water vapor permeable backsheet and a specific adhesive configuration.

Adding regions of corrugation have been disclosed as yet another method to increase flexibility or conformability of absorbent articles. EP 1088536 (Carvalho) discloses using longitudinal corrugations to provide lateral extensibility. Additionally, U.S. Pat. No. 5,607,415 (Datta et al.) purports to disclose an absorbent article having a basin-like moisture barrier with corrugations to provide an extendable region.

NZ 236101 (Hujber et al.) discloses a pants liner having a creped portion that attaches directly onto the crotch area of the wearer's pants. Parts of the liner are capable of being draped down the tubular leg portion of the pants, without any bunching or folding occurring in the creped portion of the liner.

However, the above absorbent articles are not fully flexible and do not adapt to the body as an undergarment alone does, thereby sacrificing comfort, protection and discretion. Thus, there is a need for a drapeable absorbent article that is fully flexible and adapts to the body as an undergarment alone does without sacrificing comfort, protection, and discretion. Applicants have surprisingly discovered such an absorbent article, which is described herein.

SUMMARY OF THE INVENTION

The present invention is directed to an absorbent article having a silhouette including a first end, a second end, wherein the second end being in opposite relation to the first end, and a first longitudinally extending edge opposed to a second longitudinally extending edge, the first and second longitudinally extending edges connecting the first end and the second end; and a layered portion having a body-facing layer and a garment-facing layer, wherein the absorbent article is drapeable.

In an alternate embodiment, the absorbent article also includes an absorbent layer and a transfer layer.

DETAILED DESCRIPTION OF THE INVENTION

As used herein, the terms "drapeable" and "drapability" are used interchangeably and mean having a flexural resistance of about 35 g. or less as tested by the Modified Circular Bend Test, ASTM 4032-82 as set forth in the Example section below. It has been found that, for example, cotton underwear (e.g., Hanes Cotton underwear) has a flexural resistance of less than 35 g. Drapeable articles of the present invention have also been found to have a flexural resistance of about 30 or less, about 20 or less, and about 17 or less.

As used herein, all ranges used herein expressly include at least all numbers that fall between the endpoints of ranges.

Absorbent articles of this invention have three portions: an anterior portion, a central portion, and a posterior portion and at least a body-facing layer and a garment facing layer. Any sample of the present invention taken from any portion of the entire article that includes all of the layers of the finished product is drapeable.

In one embodiment of the present invention, the absorbent article has a body facing layer and a garment facing layer. In another embodiment, the absorbent article additionally includes an absorbent layer therebetween. Other embodiments may include additional layers such as, a transfer or distribution layer, multiple layer absorbent layers and unitized versions of two or more layers.

The silhouette of absorbent articles of this invention includes those designed to fit garments having conventionally-shaped crotches, e.g., briefs and bikinis. Additionally, absorbent articles of the present invention may also be designed to fit garments having abbreviated crotches including thong, string underwear, G-string, Rio cut, Brazilian cut, etc.

The absorbent article of the present invention includes a liquid permeable layer also referred to as a body facing layer. The exterior of the body facing layer forms the body-facing surface of the absorbent article. The body facing layer may be a single layer or be made from multiple layers. The body facing layer may be formed from any fluid pervious material or combinations of materials that are comfortable against the skin and permits fluid to penetrate. For instance, the body facing layer may be a fibrous non-woven fabric made of fibers or filaments of polymers, such as polyethylene, polypropylene, polyester, or cellulose, and combinations thereof. Alternatively, the body facing layer may be formed from an apertured polymeric film. The thickness of the body facing layer may vary from about 0.001 inch (0.025 mm) to about 0.200 inch (5.000 mm), depending on the material chosen. The weight of the body facing layer material is between about 5 to about 150 gsm.

For example, any material with cloth-like features may be used for the body facing layer. Such material includes nonwoven, such as spunlace, woven, and knitted materials. In particular, spunlace material may be made from about 0 to about 100% rayon and from about 0 to about 100% polyester. The spunlace material may also be made from about 10 to about 65% rayon and from about 35 to about 90% polyester may be used. Optionally, the material used for the body-facing layer may include binders, such as thermoplastic binder fibers and latex binders.

In one embodiment, the body facing layer is a single sheet of material having a width sufficient to form the body-facing surface of the absorbent article. In another embodiment, the body facing layer has at least two layers.

The body facing layer, whether a single layer or multiple layers, may have absorbent capabilities, i.e., retains fluid. If a separate absorbent layer is used, the body facing layer may be longer and wider than the absorbent core or be of similar size as the absorbent core.

The garment facing layer of the present invention may be pliant and is typically referred to as a backsheet or barrier layer. The exterior of the garment facing layer forms the garment-facing surface of the absorbent article and, typically, is impermeable to fluids. In one embodiment, the garment facing layer may be any thin, flexible, fluid impermeable material, such as a polymeric film, e.g., polyethylene, polypropylene, or cellophane, or a normally fluid pervious material that has been treated to be impervious, such as impregnated fluid repellent paper or non-woven material, including non-woven fabric material, or a flexible foam, such as polyurethane or cross-linked polyethylene.

Additionally, the garment facing layer may be breathable, i.e., permits vapor to transpire. Known materials for this purpose include nonwoven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet.

The thickness of the backsheet when formed from a polymeric film typically is about 0.001 inch (0.025 mm) to about 0.002 inch (0.051 mm).

One embodiment of the present invention includes an absorbent layer, which may be a single layer or, alternately, be made of multiple layers. Absorbent materials used in the absorbent layer may include, but are not limited to, absorbent fibers, such as cellulose fibers, including, but not limited to wood pulp, regenerated cellulose fibers, and cotton fibers, rayon fibers and the like; superabsorbent fibers or particles; other naturally occurring absorbent materials, such as peat moss; and other synthetic absorbent materials, such as foams and the like. The absorbent layer may also include one or more of the following: thermoplastic binder fibers, latex binder, perfumes, or odor-controlling compounds or compositions. The absorbent layer may be compressed or uncompressed, embossed, or calendered. Additionally, the absorbent core may be made from any known absorbent bicomponent fibers, including those made, for example, from polyester, polyethylene, polypropylene and any combinations thereof.

The absorbent material may be woven, nonwoven, or knitted and made by any process. For example the absorbent material may be wet laid, carded, or air laid.

Absorbent articles of this invention may or may not include wings, flaps or tabs for securing the absorbent article to an undergarment.

Wings, also called, among other things, flaps or tabs, and their use in sanitary protection articles is described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly. The disclosures of these patents are incorporated herein by reference in their entirety. As disclosed in the above documents, wings are generally speaking flexible and configured to be folded over the edges of the underwear so that the wings are disposed between the edges of the underwear.

The shape of the wings may also be varied as desired. The wings may be rounded, rectangular, curvilinear, etc. The wings may be regular or irregular, symmetric or asymmetric in shape.

The overall dimensions of the absorbent article of the present invention may be as follows: a length of about 5 inches (127 mm) to 8 inches (203 mm) and a thickness of about 0.02 inch (0.5 mm) to 0.2 inch (5 mm).

Optionally, the absorbent article of the present invention may include a transfer or distribution layer. If included in the absorbent article, the transfer layer may be made of any known material that will take up fluid and then distribute and release it to an adjacent absorbent layer for storage. Transfer layers have a relatively open structure that allows for movement of fluid within the layer. Suitable materials for such transfer layers include fibrous webs, resilient foams, and the like.

The mass of materials making up the transfer layer may be absorbent, although the materials themselves are not absorbent. Thus, transfer layers that are made of hydrophobic, nonabsorbent fibers may be able to accept large volumes of fluid into interfiber void spaces while the fibers themselves do not absorb any significant quantities of fluid. Likewise, open-celled foam structures that are made from nonabsorbent materials may also absorb fluid into the cells of the foam. The walls of the cells, however, do not absorb any fluid. The cumulative spaces within the transfer layer, i.e., the interfiber void spaces in the fibrous transfer layer or the open cells in the foam transfer layer, function much like a container to hold fluid.

Typically, transfer layer fibrous webs are made of resilient, nonabsorbent materials to provide void volume and to allow for free movement of fluid through the structure. Transfer layers that are made from webs of mostly absorbent fibers absorb the fluid as it enters the structure and do not distribute it throughout the rest of the structure as efficiently as webs containing non-absorbent materials.

Adhesive is typically used to attach the layers into a single absorbent article. For example, in one embodiment, the body facing layer is attached to the barrier with adhesive HL 1491 available from H.B Fuller and Company (St. Paul, Minn.). The adhesive may be applied in any method.

Secure attachment of absorbent article of the claimed invention to the garment contributes to maintaining the feeling of the user that the absorbent article and the garment are one in the same, i.e., permits the absorbent article to move with the underwear.

The absorbent article of the present invention may be applied to the crotch by placing the garment-facing surface against the inside surface of the crotch of the garment. Various methods of attaching absorbent articles may be used. For example, chemical means, e.g., adhesive, and mechanical attachment means, e.g., clips, laces, ties, and interlocking devices, e.g., snaps, buttons, VELCRO (Velcro USA, Inc., Manchester, N.H.), zipper, and the like are examples of the various options available to the artisan.

Adhesive may include pressure sensitive adhesive that is applied as strips, swirls, or waves, and the like. As used herein, the term pressure-sensitive adhesive refers to any releasable adhesive or releasable tenacious means. Suitable adhesive compositions, include, for example, water-based pressure-sensitive adhesives such as acrylate adhesives. Alternatively, the adhesive composition may include adhesives based on the following: emulsion or solvent-borne adhesives of natural or synthetic polyisoprene, styrene-butadiene, or polyacrylate, vinyl acetate copolymer or combinations thereof; hot melt adhesives based on suitable block copoylmers—suitable block copolymers for use in the invention include linear or radial copolymer structures having the formula (A-B)x wherein block A is a polyvinylarene block, block B is a poly(monoalkenyl) block, x denotes the number of polymeric arms, and wherein x is an integer greater than or equal to one. Suitable block A polyvinylarenes include, but are not limited to Polystyrene, Polyalpha-methylstyrene, Polyvinyltoluene, and combinations thereof. Suitable Block B poly(monoalkenyl) blocks include, but are not limited to conjugated diene elastomers such as for example polybutadiene or polyisoprene or hydrogenated elastomers such as ethylene butylene or ethylene propylene or polyisobutylene, or combinations thereof. Commercial examples of these types of block copolymers include Kraton™ elastomers from Shell Chemical Company, Vector™ elastomers from Dexco, Solprene™ from Enichem Elastomers and Stereon™ from Firestone Tire & Rubber Co.; hot melt adhesive based on olefin polymers and copolymers where in the olefin polymer is a terpolymer of ethylene and a co-monomers, such as vinyl acetate, acrylic acid, methacrylic acid, ethyl acrylate, methyl acrylate, n-butyl acrylate vinyl silane or maleic anhydride. Commercial examples of these types of polymers include Ateva (polymers from AT plastics), Nucrel (polymers from DuPont), Escor (from Exxon Chemical).

Where adhesive is used, a release strip may be applied to protect the adhesive on the absorbent article prior to attaching the absorbent article to the crotch. The release strip can be formed from any suitable sheet-like material adheres with sufficient tenacity to the adhesive to remain in place prior to use but which can be readily removed when the absorbent article is to be used. Optionally, a coating may be applied to release strip to improve the ease of removability of the release strip from the adhesive. Any coating capable of achieving this result may be used, e.g., silicone.

Any or all of the cover, absorbent layer, transfer layer, backsheet layer, and adhesive layers may be colored. Such coloring includes, but is not limited to, white, black, red, yellow, blue, orange, green, violet, and mixtures thereof. Color may be imparted according the present invention through dying, pigmentation, and printing. Colorants used according the present invention include dyes and inorganic and organic pigments. The dyes include, but are not limited to, anthraquinone dyes (Solvent Red 111, Disperse Violet 1, Solvent Blue 56, and Solvent Green 3), Xanthene dyes (Solvent Green 4, Acid Red 52, Basic Red 1, and Solvent Orange 63), azine dyes (Jet black), and the like.

Inorganic pigments include, but are not limited to, titanium dioxide (white), carbon black (black), iron oxides (red, yellow, and brown), chromium oxide (green), ferric ammonium ferrocyanide (blue), and the like.

Organic pigments include, but are not limited to diarylide yellow AAOA (Pigment Yellow 12), diarylide yellow AAOT (Pigment Yellow 14), phthalocyanine blue (Pigment Blue 15), lithol red (Pigment Red 49:1), Red Lake C (Pigment Red), and the like.

The absorbent article may include other known materials, layers, and additives, such as, foam, net-like material, perfumes, medicaments or pharmaceutical agents, moisturizers, odor control agents, and the like. The absorbent article can optionally be embossed with decorative designs.

The absorbent article may be packaged as unwrapped absorbent articles within a carton, box or bag. The consumer withdraws the ready-to-use article as needed. The absorbent article may also be individually packaged (each absorbent article encased within an overwrap).

Also contemplated herein include asymmetrical and symmetrical absorbent articles having parallel longitudinal edges, dog bone- or peanut-shaped, and the like.

From the foregoing description, one skilled in the art can ascertain the essential characteristics of this invention, and without departing from the spirit and scope thereof, can make various changes and modifications. Embodiments set forth by way of illustration are not intended as limitations on the variations possible in practicing the present invention.

EXAMPLE

Samples of commercially available pantiliners were compared to samples of the present invention and samples from the crotch portion of an undergarment.

Peak bending stiffness is determined by a test that is modeled after the ASTM D 4032-82 CIRCULAR BEND PROCEDURE, the procedure being considerably modified and performed as follows. The CIRCULAR BEND PROCEDURE is a simultaneous multi-directional deformation of a material in which one face of a specimen becomes concave and the other face becomes convex. The CIRCULAR BEND PROCEDURE gives a force value related to flexural resistance, simultaneously averaging stiffness in all directions.

The apparatus necessary for the CIRCULAR BEND PROCEDURE is a modified Circular Bend Stiffness Tester, having the following parts:

1. A smooth-polished steel plate platform, which is 102.0 mm by 102.0 by 6.35 mm having an 18.75 mm diameter orifice. The lap edge of the orifice should be at a 45 degree angle to/a depth of 4.75 mm;

2. A plunger having an overall length of 72.2 mm, a diameter of 6.25 mm, a ball nose having a radius of 2.97 mm and a needle-point extending 0.88 mm therefrom having a 0.33 mm base diameter and a point having a radius of less than 0.5 mm, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), than the needle-point should not be used. The bottom of the plunger should be set well above the top of the orifice plate. From this position, the downward stroke of the ball nose is to the exact bottom of the plate orifice;

3. A force-measurement gauge and more specifically an Instron inverted compression load cell. The load cell has a load range of from about 0.0 to about 2000.0 g;

4. An actuator and more specifically the Instron Model No. 1122 having an inverted compression load cell. The Instron 1122 is made by the Instron Engineering Corporation, Canton, Mass.

In order to perform the procedure for this test, as explained below, five representative samples for each article are necessary. From each of the five samples to be tested, some number "Y" of 37.5 mm by 37.5 mm test specimens are cut. For undergarments, the crotch portion was made from at least one layer. For absorbent articles, test specimens were cut from anterior portion, the central portion, and the posterior portion. This test is directed to the overall drapeability of the article and not merely the peripheral portions thereof and, therefore, the drapeability of the present invention is more concerned with the drapeability of the entire article than any specific portion thereof.

The test specimens should not be folded or bent by the test person, and the handling of specimens must be kept to a minimum and to the edges to avoid affecting flexural-resistance properties.

The procedure for the CIRCULAR BEND PROCEDURE is as follows. The specimens are conditioned by leaving them in a room that is 21° C., +/−0.1° C. and 50%, +/−2.0%, relative humidity for a period of two hours. The plunger speed is set at 50.0 cm per minute per full stroke length. A specimen is centered on the orifice platform below the plunger such that the body facing layer of the specimen is facing the plunger and the barrier layer of the specimen is facing the platform. The indicator zero is checked and adjusted, if necessary. The plunger is actuated. Touching the specimen during the testing should be avoided. The maximum force reading to the nearest gram is recorded. The above steps are repeated until all of the specimens have been tested.

CALCULATIONS

The peak bending stiffness for each specimen is the maximum force reading for that specimen. Remember that "Y" number of sets of five samples were cut. The values received for each specimen were averaged. The flexural resistance for an article is the average peak bending stiffnesses for all "Y" specimens taken from each sample of that article.

TABLE 1

| Sample Number | Average Peak Load (grams) | Percent Standard Deviation |
|---|---|---|
| Commercially Available Underwear Sample 1 | 2.17 | 8.91 |
| Commercially Available Underwear Sample 2 | 2.83 | 12.37 |
| Commercially Available Underwear Sample 3 | 4.78 | 30.57 |
| Inventive Sample 1 | 17.07 | 10.8 |
| Inventive Sample 2 | 17.56 | 8.00 |
| Inventive Sample 3 | 27.58 | 18.5 |
| Comparative Sample 1 | 46.21 | 12.8 |
| Comparative Sample 2 | 49.56 | 7.9 |
| Comparative Sample 3 | 127.02 | 14.1 |
| Comparative Sample 4 | 150.87 | 9.1 |
| Comparative Sample 5 | 173.26 | 8.2 |
| Comparative Sample 6 | 256.58 | 7.9 |
| Comparative Sample 7 | 286.72 | 9.1 |

Commercially Available Underwear Sample 1 Hanes Her Way 100% Nylon with 100% Cotton Crotch (Grey) This article had two crotch layers, one was nylon and body-facing layer was cotton, which were not bonded together. Only the body-facing layer was tested.

Commercially Available Underwear Sample 2 Hanes Her Way 100% Nylon (black) ribbed crotch. This article had one crotch layer.

Commercially Available Underwear Sample 3 Fruit of the Loom 100% cotton jersey (cream colored). This article had two crotch layers, both were cotton. Only layer was tested.

Inventive Sample 1 having a 75 gsm spunlace body facing layer made from 75% polyester and 25% rayon (3P075V25P75 from Spuntech Industries Ltd., Upper Tiberias, Israel) and a 30 gsm microporous polyethylene backsheet (01030A1-1-1-1-2, FullSafe, Manila, Philippines).

Inventive Sample 2 having a 75 gsm spunlace body facing layer made from 75% polyester and 25% rayon (LBN040, from PGI, Benson, N.C.) and a 30 gsm microporous polyethylene backsheet (01030A1-1-1-1-2, FullSafe, Manila, Philippines).

Inventive Sample 3 having a 55 gsm spunlace body facing layer made from 35% polyester and 65% rayon (LIDRO 356355-Jacob Holm Industries S.A.S, Soultz, France), and a three-layer absorbent core made from three layers (first layer: 10 gsm 100% PET/PE, second layer: 15 gsm 66% PET/PE/ 34% rayon and third layer: 15 gsm 66 PET/PE/34% rayon) (JS40-1, Kang Na Hsiuing Enterprise Company, Ltd., Taipei, Taiwan), and a 30 gsm microporous polyethylene backsheet (01030A-1-1-1-1-2, FullSafe, Manila, Philippines).

Comparative Samples 1-7 were samples of pantiliners commercially available.

| Sample number | Commercial Product Name (date code) |
|---|---|
| Comparative Sample 1 | Sofy Regular Pantiliner |
| Comparative Sample 2 | Sofy Breathable (00120702123) |
| Comparative Sample 3 | Kotex Lightdays (LF101002C) |
| Comparative Sample 4 | Carefree Ultrathins |
| Comparative Sample 5 | Carefree Body Shape (1996M02341) |
| Comparative Sample 6 | Carefree (Europe) (1057A) |
| Comparative Sample 7 | Procter & Gamble Alldays Freshweave (0344CA11762040B) |

What is claimed is:

1. An absorbent article consisting of:
   a liquid permeable cover layer;
   a liquid impermeable barrier layer;
   wherein the entire absorbent article has a flexural resistance of less than 30 g; and
   wherein the entire absorbent article has a thickness of about 0.5 mm to about 5.0 mm.

2. An absorbent article consisting of:
   a liquid permeable cover layer;
   a liquid impermeable barrier layer;
   wherein the entire absorbent article has a flexural resistance of about 20 g or less; and
   wherein the entire absorbent article has a thickness of about 0.5 mm to about 5.0 mm.

3. The absorbent article according to claim 2, wherein the entire absorbent article has a flexural resistance of about 17 g or less.

* * * * *